(12) United States Patent
Park et al.

(10) Patent No.: US 9,993,250 B2
(45) Date of Patent: Jun. 12, 2018

(54) DEVICE FOR PROTECTING THE RECTAL ANASTOMOSIS

(71) Applicants: KYUNGPOOK NATIONAL UNIVERSITY INDUSTRY—ACADEMIC COOPERATION FOUNDATION, Daegu (KR); KYUNGPOOK NATIONAL UNIVERSITY HOSPITAL, Daegu (KR)

(72) Inventors: Jun Seok Park, Daegu (KR); Gyu Seog Choi, Daegu (KR)

(73) Assignees: KYUNGPOOK NATIONAL UNIVERSITY INDUSTRY-ACADEMIC COOPERATION FOUNDATION, Daegu (KR); KYUNGPOOK NATIONAL UNIVERSITY HOSPITAL, Daegu (KR)

( * ) Notice: Subject to any disclaimer, the term of this patent is extended or adjusted under 35 U.S.C. 154(b) by 755 days.

(21) Appl. No.: 14/575,303

(22) Filed: Dec. 18, 2014

(65) Prior Publication Data

US 2015/0174385 A1 Jun. 25, 2015

(30) Foreign Application Priority Data

Dec. 19, 2013 (KR) .......................... 10-2013-0159447

(51) Int. Cl.
*A61M 3/02* (2006.01)
*A61M 1/00* (2006.01)
(Continued)

(52) U.S. Cl.
CPC ...... *A61B 17/1114* (2013.01); *A61B 17/1204* (2013.01); *A61B 17/12036* (2013.01);
(Continued)

(58) Field of Classification Search
CPC .................. A61F 5/4405; A61F 5/442; A61M 2210/1064; A61M 2210/1067
See application file for complete search history.

(56) References Cited

U.S. PATENT DOCUMENTS 3,053,257 A * 9/1962 Birtwell ............ A61M 25/0017
604/916
3,509,884 A 5/1970 Bell
(Continued)

FOREIGN PATENT DOCUMENTS

CN 2160401 Y 4/1994
JP H0241154 A 2/1990
(Continued)

*Primary Examiner* — Susan Su
(74) *Attorney, Agent, or Firm* — Clark & Elbing LLP; Susan M. Michaud

(57) ABSTRACT

The present invention relates to a device for protecting rectal anastomosis. The device of the present invention is a double type leakage prevention system composed of micro-villi of a head filter and a triple lumen catheter, and thus minimizes contamination of the anastomotic area from intestinal contents, thereby enabling successful healing of the rectal anastomotic area. The device of the present invention has a main tube with side holes, and thus the intestinal contents, even when passing through the head filter, are sucked into the main tube through the side holes, so that the intestinal contents can be effectively drained while being diverted from the anastomotic area. The device of the present invention is inserted through the anus after surgery and thus involves less risk of additional complications due to the installation of the device, and has advantages of low manufacturing costs due to the simplification of the structure and convenient use and handling. Furthermore, the device of the present invention serves as an existing support for protecting anastomosis, thereby alleviating patient discomfort due to anastomotic leakage.

20 Claims, 14 Drawing Sheets

(51) Int. Cl.
  *A61B 17/11* (2006.01)
  *A61B 17/12* (2006.01)
  *A61F 5/00* (2006.01)
  *A61F 5/44* (2006.01)
  *A61F 5/441* (2006.01)
  *A61F 5/443* (2006.01)
  *A61F 5/451* (2006.01)
  *A61B 17/00* (2006.01)
  *A61B 17/30* (2006.01)

(52) U.S. Cl.
  CPC ...... *A61B 17/12136* (2013.01); *A61F 5/0093* (2013.01); *A61F 5/441* (2013.01); *A61F 5/443* (2013.01); *A61F 5/4405* (2013.01); *A61F 5/451* (2013.01); *A61B 2017/00818* (2013.01); *A61B 2017/306* (2013.01); *A61M 2205/75* (2013.01); *A61M 2210/1064* (2013.01)

(56) References Cited

U.S. PATENT DOCUMENTS

| | | | | |
|---|---|---|---|---|
| 4,596,554 A * | 6/1986 | Dastgeer | ............... | A61F 5/00 604/101.05 |
| 4,772,260 A * | 9/1988 | Heyden | ............ | A61M 25/0068 604/103.03 |
| 5,335,669 A * | 8/1994 | Tihon | ............... | A61B 5/01 600/549 |
| 6,840,923 B1 * | 1/2005 | Lapcevic | ............ | A61F 5/442 604/19 |
| 6,843,766 B1 * | 1/2005 | Nemir | ............... | A61F 2/0013 600/31 |
| 2002/0019613 A1 * | 2/2002 | Alexandersen | ..... | A61M 3/0241 604/279 |
| 2004/0039348 A1 * | 2/2004 | Kim | ............... | A61M 3/0241 604/264 |
| 2005/0004533 A1 * | 1/2005 | Smith | ............... | A61M 3/0283 604/275 |
| 2005/0033226 A1 * | 2/2005 | Kim | ............... | A61F 2/0013 604/101.01 |
| 2005/0054996 A1 * | 3/2005 | Gregory | ............ | A61F 5/445 604/317 |
| 2006/0100595 A1 * | 5/2006 | von Dyck | .......... | A61B 5/14503 604/348 |
| 2007/0276189 A1 | 11/2007 | Abel et al. | | |
| 2011/0218389 A1 * | 9/2011 | Gobel | ............... | A61M 25/1002 600/32 |
| 2011/0282311 A1 | 11/2011 | Nishtala | | |
| 2012/0296272 A1 | 11/2012 | Bidault et al. | | |
| 2013/0116559 A1 * | 5/2013 | Levin | ............... | A61M 3/0279 600/437 |
| 2014/0052063 A1 * | 2/2014 | Gregory | ............ | A61M 25/10187 604/99.03 |
| 2014/0276502 A1 * | 9/2014 | Cisko | ............... | A61F 5/4408 604/355 |

FOREIGN PATENT DOCUMENTS

| | | |
|---|---|---|
| JP | H04-200470 A | 7/1992 |
| JP | H09-253112 A | 9/1997 |
| JP | 2009-291632 A | 12/2009 |
| JP | 2013-500751 A | 1/2013 |
| WO | WO-02/26293 A1 | 4/2002 |
| WO | WO-2011/012323 A1 | 2/2011 |
| WO | WO-2013/074763 A1 | 5/2013 |

* cited by examiner

Stopper　　　　　Tape terminal end of the main tube

Ballooning Check Valve      Suction Hole

DEVICE FOR PROTECTING THE RECTAL ANASTOMOSIS

FIELD OF THE INVENTION

The present invention relates to a device for protecting the rectal anastomosis

BACKGROUND ART

Anastomotic leakage is the most dangerous and serious complication of rectal cancer surgery, and is known to occur in 10-20% of surgical patients. Anastomotic leakage causes a long period of hospitalization and a subsequent increase in medical expenses. Moreover, there are advanced research findings that anastomotic leakage may cause long-term rectal dysfunction, and is associated with local tumor recurrence in terms of oncology.

There is currently no appliance which has been clinically verified to be a help to prevent rectal anastomotic leakage. However, some surgeons have used rectal tubes which can be inserted through the anus, with the purpose of protecting anastomoses. Most of these appliances have a long thin tube shape, and are made of a latex material. The rectal tubes are known to protect the anastomotic area through a mechanism in which the pressure of the anal sphincter is lowered to reduce the pressure in the lower rectal canal. However, existing normal rectal tubes are originally devised to assist with enemas for constipation patients, and thus are insufficient in effectively protecting the anastomotic area. Most of all, the technical limitation is that there are no devices capable of effectively filtering or diverting intestinal contents which flow into the anastomotic area.

The present invention is for reducing complications due to the rectal anastomotic leakage after surgery. Until now, the only way to effectively prevent anastomotic leakage was to create an artificial anus (ileal fistula or colorectal fistula). This temporary intestinal fistula protects the anastomotic area from the intestinal contents, and thus is helpful in successively stabilizing the anastomotic area. However, the temporary intestinal fistula has several serious problems, such as its own complications, patient discomfort, complications due to colostomy closure, and additional costs.

Meanwhile, the appliances used to prevent anastomotic leakage are sewed on the anus region using sutures to be fixed to the patient body, which continuously causes the patient's pain after surgery. Thus, the present inventors have invented a separate attachable type fixing device as a less invasive manner in order to alleviate the patient's pain, and the device of the present invention is fixed by being simply attached to the patient's body.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DETAILED DESCRIPTION OF THE INVENTION

Technical Problem

The present inventors have endeavored to develop a device for protecting rectal anastomosis, the device being capable of successfully healing the wounds of the rectal anastomosis by diverting the intestinal contents from the newly formed rectal anastomosis after rectal surgery. As a result, the present inventors have developed a device for protecting rectal anastomosis, capable of preventing the direct inflow of the intestinal contents into the anastomosis area using a head filter with micro-villi, wherein side holes are formed in a main tube of the device, and thus the intestinal contents are sucked into the main tube through the side holes even though the intestinal contents pass through the head filter. The present inventors have found that the intestinal contents can be effectively drained while being diverted from the anastomotic area, and completed the present invention.

An aspect of the present invention is to provide a. Other purposes and advantages of the present invention will become clarified by the following detailed description of invention, claims, and drawings.

Technical Solution

In accordance with an aspect of the present invention, there is provided a device for protecting rectal anastomosis comprising:

(a) a cylinder- or tube-shaped head filter which is slanted toward an outer head portion of a main tube and can be inflated by pressure; and (b) a main tube which can be inserted inside the intestinal canal and includes a main duct, through which the intestinal contents pass, and a first auxiliary duct which transfers pressure for inflating the head filter.

The present inventors have endeavored to develop a device for protecting rectal anastomosis, the device being capable of successfully healing the wounds of the rectal anastomosis by diverting the intestinal contents from the newly formed rectal anastomosis after rectal surgery. As a result, the present inventors have developed a device for protecting rectal anastomosis, capable of preventing the direct inflow of the intestinal contents into the anastomosis area using a head filter with micro-villi, wherein side holes are formed in a main tube of the device, and thus the intestinal contents are sucked into the main tube through the side holes even though the intestinal contents pass through the head filter. The present inventors have found that the intestinal contents can be effectively drained while being diverted from the anastomotic area, and completed the present invention.

Hereinafter, the device for protecting rectal anastomosis will be described as below.

Component (a): Head Filter (110)

The device of the present invention includes a head filter which is slanted toward an outer head portion of a main tube. The head filter has a cylinder or tube shape which can be inflated by pressure, and preferably has a cylinder or tapered shape of which the width widens toward the bottom.

The head filter is positioned at the outer head portion of the main tube. The head filter may be positioned between side holes (see FIG. 4) or behind the side holes (see FIG. 5) when side holes are formed in the main tube.

The device of the present invention is invented to minimize the direct inflow of the intestinal contents into the anastomotic area by installing a head filter, which can be inflated by pressure, at the head portion of the main tube. The inflatable head filter is formed of a polymeric compound containing polyurethane or the like, and thus 1) can be freely inflated and deflated by being installed in the rectum and then controlled by air pressure; 2) can retain its original shape without being sucked into the intestine for a predetermined period of time; and 3) can primarily filter intestinal contents in the intestine with a small diameter since the surface of the head filter is formed in a shape of micro-villi or micro-corrugations.

Meanwhile, the head filter may have a shape of which the width widens toward the bottom (in a direction opposite to the direction into which the device of the present invention is inserted) when the head filter is inflated by pressure. Since the volume inflation by air is greater in a lower part of the head filter than an upper part of the head filter, the cross-section of the head filter is shown to have a trapezoidal shape.

According to the present invention, the area of the head portion (or upper part) of the head filter is greater than that of the tail portion (or lower part) of the head filter. The device of the present invention is inserted through the anus of the patient, and thus it is important that the patient does not feel discomfort at the time of insertion. In cases where the area of the head portion of the head filter is smaller than that of the tail portion of the head filter, the head filter can be smoothly inserted into the body of the patient.

According to the present invention, the air-inflatable head filter is moved into the human body and then inflated, and thus needs to be formed of a fluidal or elastic material such as biocompatibility polymers comprising polyurethane (PU), polyester (PE), polyvinylchloride (PVC), polytetrafluoroethylene (PTFE), polyethersulfone (PES), polyethylene (PE), polyetherimide (PEI), polycarbonate (PC), polyetheretherketone (PEEK), polysulfone (PS) and polypropylene (PP); silicones or rubber, but are not limited to thereof. In cases where the head filter is formed of a polymeric compound, the head filter is neither sucked nor chemically transformed while the head filter is positioned in the anus or rectum within days. In addition, the head filter has good elasticity and thus can be naturally inflated by air. Therefore, the head filter has few side effects due to the suction into the body or filter perforation, and thus is very safe.

The diameter of the head filter is about 20 mm to 35 mm before inflation by pressure, and according to the present invention, the diameter of the head filter before inflation may be 22 mm to 32 mm or 25 mm to 30 mm. The diameter of the head filter after inflation is about 35 mm to 55 mm, and according to the present invention, the diameter of the head filter after inflation may be 38 mm to 52 mm or 40 mm to 50 mm. Meanwhile, the entire length of the head filter is 1 mm to 30 mm.

The head filter can be inflated by pressure, for example, air pressure or water pressure. According to the present invention, the head filter may be inflated by air pressure.

The head filter is elastic, and thus, when the head filter is installed in the rectal tube and air is injected into the head filter, the volume of the head filter is increased by approximately 20-40%, thereby efficiently forming a barrier.

Component (b): Main Tube (120)

In addition, the device of the present invention can be inserted into the intestinal tube, and has a main tube 120 including a main duct 121, through which intestinal contents can pass, and a first auxiliary duct 122 capable of transferring pressure for inflating the head filter 110.

The main tube may have side holes 130 formed in the outer circumferential surface, wherein intestinal contents can pass through the side holes 130.

The main tube may include in the device for protecting rectal anastomosis may further include a second auxiliary duct 123 in addition to the main duct and the first auxiliary duct 122 (double or triple lumen tube) That is, an auxiliary duct having a negative pressure drainage function is installed in the rectal tube, and thus some intestinal contents passing through the head filter can be secondarily sucked. The second auxiliary duct among triple lumens communicates with the side holes of the body of the main tube, and can be connected with a negative pressure pump outside the anus. That is, the second auxiliary duct may be manufactured integrally with or separately from the main tube, and in this case, the device of the present invention may be a double lumen tube or a triple lumen tube. The first auxiliary duct among the triple lumens may be connected with an air injector for balloon dilation of the tail portion of the main tube. When air of approximately 5-30 cc is injected through the second auxiliary duct, the head filter connected to the head portion of the main tube is inflated through a balloon dilation mechanism, thereby forming a barrier.

According to the present invention, a hole which communicates with the inside of the head filter may be formed in the main tube, so that the intestinal contents flowing in through the head filter can be moved into the main tube (see FIG. 3). Some of micro-sized intestinal contents are likely to flow into the head filter, and in order to prevent this, holes connected to the main duct 121 or the second auxiliary duct 123 may be formed outside the main tube.

Multiple side holes may be formed in the outer circumferential surface of the main tube, and the side holes may be arranged in a line on both sides of the main tube. The side holes arranged in a line on both sides of the main tube are alternately arranged such that the side holes neither go through each other nor face each other. This arrangement, when the intestinal contents enter through the side holes on one side of the main tube, prevents the re-leakage of the intestinal contents through side holes of the other side that face the side holes on one side in straight lines.

The main tube may penetrate the head filter to protrude above the head filter. Thus, the intestinal contents can be sucked into the main tube more easily. One to six side holes 130 through which the intestinal contents can pass may be formed in the protruding portion of the main tube. For example, when the side holes are arranged in a line on both sides of the main tube, one to three side holes may be formed on each side of the main tube.

Six to twelve side holes may be additionally formed in the main tube below the head filter. For example, when the side holes are arranged in a line on both sides of the main tube, three to six side holes are formed on each side of the main tube. Meanwhile, in cases where the intestinal contents are sucked through the side holes positioned above the head filter, some of the intestinal contents are likely to be released through the side holes positioned below the head filter, which can be prevented by an additional support device.

In cases where there are more side holes than the above-mentioned number, the main tube itself may be bent and thus the device is difficult to operate. Therefore, the number of side holes formed in the main tube needs to be smaller than a certain number.

The diameter of the main tube is approximately 15 mm to 35 mm, and according to the present invention, the diameter may be 20 mm to 30 mm or 25 mm to 28 mm. Meanwhile, the entire length of the main tube is 150 mm to 300 mm, and the protruding portion of the head filter after penetrating the head filter is approximately 10 mm to 30 mm.

The overall main tube may be formed of a hard material or a soft material and may be manufactured to contain both the hard material and the soft material. For example, when the main tube is manufactured to contain both the hard material and the soft material, a predetermined portion of the main tube, which is inserted into the body of the patient, is formed of the soft material, and a portion of the main tube, which is manipulated by a worker outside the body, is formed of the hard material. Meanwhile, the main tube may be manufactured in a straight line, but may be bent at a gentle slope of about 10 to 30 degrees. When a straight line type main tube is inserted into the body of the patient, the main tube is difficult to accurately insert into the rectal tube due to the anatomical structure of the patient. For example, the main tube may be manufactured such that the main tube is bent at a slope from about 15 m below the head filter.

The main tube may have multiple grooves for the combination with a pad as a fixing instrument. When the multiple grooves are formed in the main tube, the main tube has directivity in all directions and thus can be bent in a predetermined direction according to the operation of the worker.

In cases where the fixing tool 160 is a pad, the pad has a circular shape of which the center portion is concave (or convex), and protrusions are formed on a lower surface (opposite side of the convex surface) of the pad or on the inside of the pad which is in contact with the main tube, so that the pad can be combined with the grooves of the main tube.

In the device for protecting rectal anastomosis, the pressure for inflating the head filter is supplied from the outside. According to the present invention, the pressure is air pressure, and thus the device of the present invention may further include an air injector (e.g., syringe).

Air or the like is moved into the head filter through the first auxiliary duct 122, and a valve for preventing the backflow of air or the like may be formed at the terminal end of the first auxiliary duct. For example, a check valve 125 may be formed at the terminal end of the first auxiliary duct, and the check valve is designed to have a valve of a soft material (rubber or silicon) therein, wherein air cannot pass through the valve at normal times, but an air pusher of a hard material (plastic, etc.) can be inserted through the valve.

Meanwhile, the device for protecting rectal anastomosis may further include a negative pressure pump for providing a pressure for sucking out the intestinal contents.

In addition, the device for protecting rectal anastomosis may further include a storage unit for accommodating the intestinal contents sucked out through the main tube. A pack (e.g., drainage pack) or a container, which is used to accommodate the intestinal contents, is generally used as the storage unit. The negative pressure pump which can be installed near the patient bed may be connected with the main tube (the main duct, or the main duct and the second auxiliary duct) for the use thereof.

In the conventional art, the appliances used to protect rectal anastomosis were sewed on the anus region using sutures so as to be fixed to the body of the patient, which continuously caused the patient's pain after surgery. However, the device of the present invention is fixed by being simply attached to the body of the patient using a separate attach type fixing tool.

According to the present invention, the device for protecting rectal anastomosis of the present invention may further include a fixing tool 160 for fixing the main tube outside the intestinal tube. The fixing tool 160 may be, for example, a radial-shaped sticker with an adhesive surface, or a pad. In addition, the device of the present invention may further include a stopper 170 for preventing the up-and-down movement of the fixing tool 160.

The stopper may be installed on the outer circumferential surface of the main tube, and the number of stopper installing locations 124 on the outer circumferential surface of the main tube is one or more. The degree at which the main tube is inserted varies according to the difference between individual patients, and the stopper is more pushed toward the tail portion of the main tube for a patient in need of more insertion. The stopper prevents the movement of the fixing tool 160, and a cylinder-shaped passage is formed in the center portion of the stopper such that the main tube can penetrate the stopper (see FIG. 9).

In cases where the fixing tool 160 is a pad, the pad has a circular shape of which the center portion is concave (or convex), and protrusion are formed on a lower surface (opposite side of the convex surface) of the pad or on an inside of the pad which is in contact with the main tube, so that the pad can be combined with the grooves of the main tube.

The device for protecting rectal anastomosis of the present invention may further include a radial-shaped rectal inner wall suction preventing tool installed on the foremost portion of the main tube, wherein the rectal inner wall suction preventing tool prevents the obstruction of the movement of the intestinal contents, which is caused by blocking the side holes of the main tube by the rectal inner wall According to an embodiment of the present invention, the rectal inner wall suction preventing tool is approximately cylindrical in shape, but may have a cylinder shape of which the width widens toward the bottom, or a tapered shape, for improving the insertion efficiency into the anastomotic area. Side holes are formed in a side surface of the tapered shape to additionally help with the suction of the intestinal contents. Meanwhile, the rectal inner wall suction preventing tool has a hole formed in the central portion, so that the main tube can penetrate the rectal inner wall suction preventing tool. Here, the main tube may penetrate the rectal inner wall suction preventing tool and protrude above the rectal inner wall suction preventing tool by about 1 cm to 2 cm.

The use of the device of the present invention will be described as below. Immediately after the rectal anastomosis surgery, the main tube is allowed to move above the anastomotic area through the anus. After the main tube is positioned to be fixed, a balloon is dilated through the air injector of the second auxiliary duct. The head filter installed on the head portion of the main tube is inflated, and then generally positioned above from the anastomotic area by 5 cm to 7 cm, and thus primarily blocks the intestinal contents. The intestinal contents passing through the primary barrier are sucked into the main tube through the side holes formed in the body of the main tube.

The device of the present invention is removed 4-5 days after surgery, depending on the clinical results of the patient. When the initially injected air is expelled through the air injector at the time of removing the device, the device can be easily pulled out toward the anus without damaging the anastomotic area. The air injector can easily inject air through a 10 cc-general syringe or the like. In addition, when an empty syringe is connected to the first auxiliary for the removal of air, the air is automatically expelled.

According to the present invention, a backflow prevention valve is formed at the terminal end of the first auxiliary duct into which air can be injected. For example, as shown in FIGS. 11 and 12, a check valve including the backflow prevention valve may be installed on the terminal end of the first auxiliary duct. An air gateway is formed at the terminal end of the check valve into which a syringe without a needle is inserted. The check valve is composed of an air pusher 1, a silicone valve 2, a tube 3, a tube holder 4, and a valve cover 5 (see FIG. 13). When the syringe is inserted into the air gateway to apply pressure toward the silicone valve, the air pusher penetrates the silicone valve and then is put on the center of the silicon valve. The air pusher has a cylinder shape, and a passage through which air can pass is formed inside the air pusher, and thus the moment that the air pusher is inserted into the silicone valve to push air inside the cylinder, the air in the syringe is moved into the first auxiliary duct through the air gateway. Thus, the head filter is inflated by the air. Meanwhile, when the syringe inserted into the air gateway is removed, the air pusher is again pushed out from the silicone valve and the air inserted into the head filter does not leak out by the silicone valve.

The outstanding feature of the present invention is a double type leakage prevention system composed of micro-villi of the head filter and a double lumen catheter. Anastomotic leakage after a rectorectostomy procedure mostly occurs within 3-5 days after the surgery. Therefore, if the intestinal contents are drained from the body without passing through the rectal anastomotic area, the fatal consequences such as anastomotic leakage can be significantly reduced. The present invention is directed to a device capable of filtering the intestinal contents through the head filter installed on an inflatable collection duct and a double lumen catheter of the main tube, wherein the intestinal contents passing through the primary barrier are sucked into the double lumen catheter through the side holes. This two-step defense system minimizes contamination from the intestinal contents, and helps to successfully heal the rectal anastomotic area that was just formed.

Features and advantages of the present invention are summarized as follows:

(a) The present invention relates to a device for protecting rectal anastomosis.

(b) The device of the present invention is a double type leakage prevention system composed of micro-villi of a head filter and a triple lumen catheter, and thus minimizes contamination of the anastomotic area from intestinal contents, thereby enabling successful healing of the rectal anastomotic area.

(c) The device of the present invention has a main tube with side holes, and thus the intestinal contents, even when passing through the head filter, are sucked into the main tube through the side holes, so that the intestinal contents can be effectively drained while being diverted from the anastomotic area.

(d) The device of the present invention is inserted through the anus after surgery and thus involves less risk of additional complications due to the installation of the device, and has advantages of low manufacturing costs due to the simplification of the structure and convenient use and handling. Furthermore, the device of the present invention serves as an existing support for protecting anastomosis, thereby alleviating patient discomfort due to anastomotic leakage.

BRIEF DESCRIPTION OF THE DRAWINGS

The above and other objects, features and advantages of the present invention will be more apparent from the following detailed description taken in conjunction with the accompanying drawings, in which.

Figure 1:
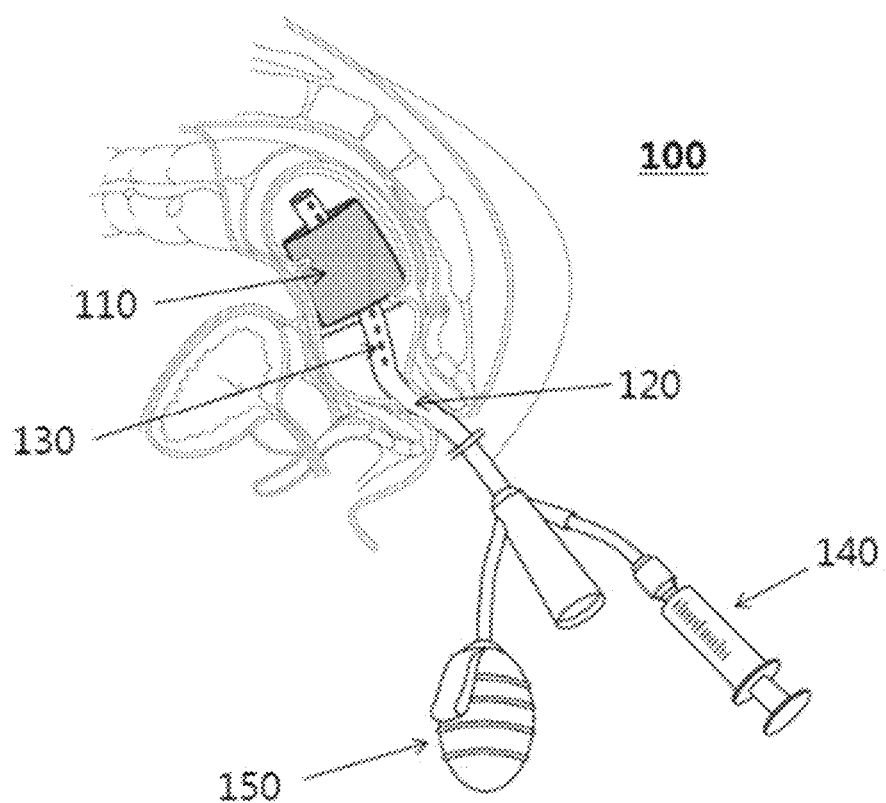
FIG. 1 shows that a device of the present invention is placed in the intestinal canal—A head filter is inflated to stay in the intestinal canal, and the tail portion of the device is connected with a negative pressure pump and a syringe for air injection.

100: a device for protecting rectal anastomosis
110: a head filter
111: micro-villi
120: a main tube
121: a main duct
122: a first auxiliary duct
123: a second auxiliary duct
124: stopper mounting part
125: check valve
126: groove
130: side hole
140: syringe
150: a negative pressure pump
160: a fixing tool
170: stopper
180: a rectal inner wall suction preventing tool

DETAILED DESCRIPTION OF THE PREFERRED EMBODIMENTS

Hereinafter, the present invention will be described in detail with reference to examples. These examples are only for illustrating the present invention more specifically, and it will be apparent to those skilled in the art that the scope of the present invention is not limited by these examples.

EXAMPLES

Hereinafter, the present invention will be described as below with reference to accompanying drawings.

Figure 3:
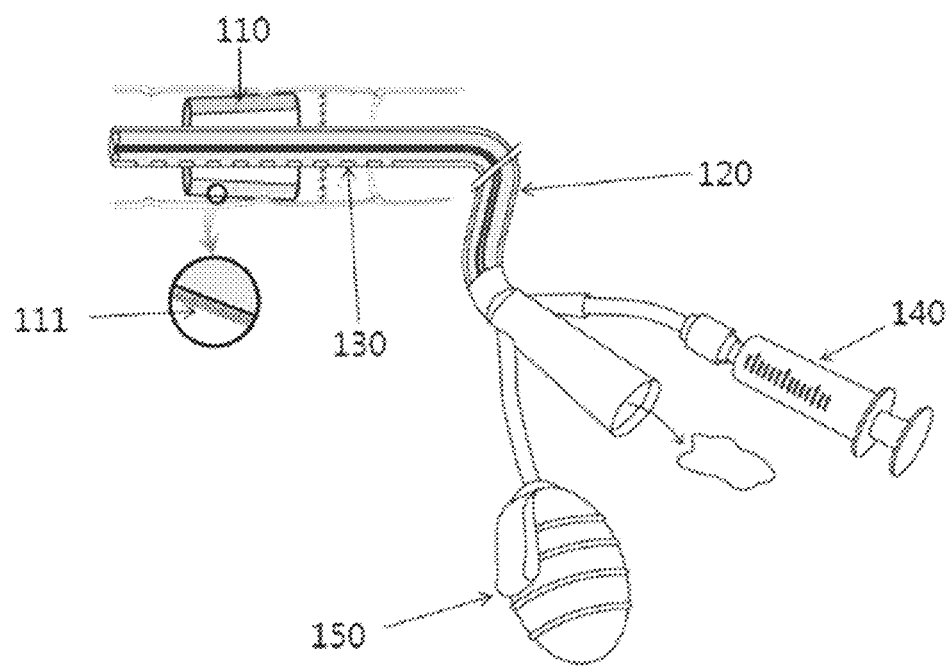
FIG. 3 shows that a device of the present invention is placed in the intestinal canal—A small circle shows a magnified view of a surface of the head filter.
Figure 4:
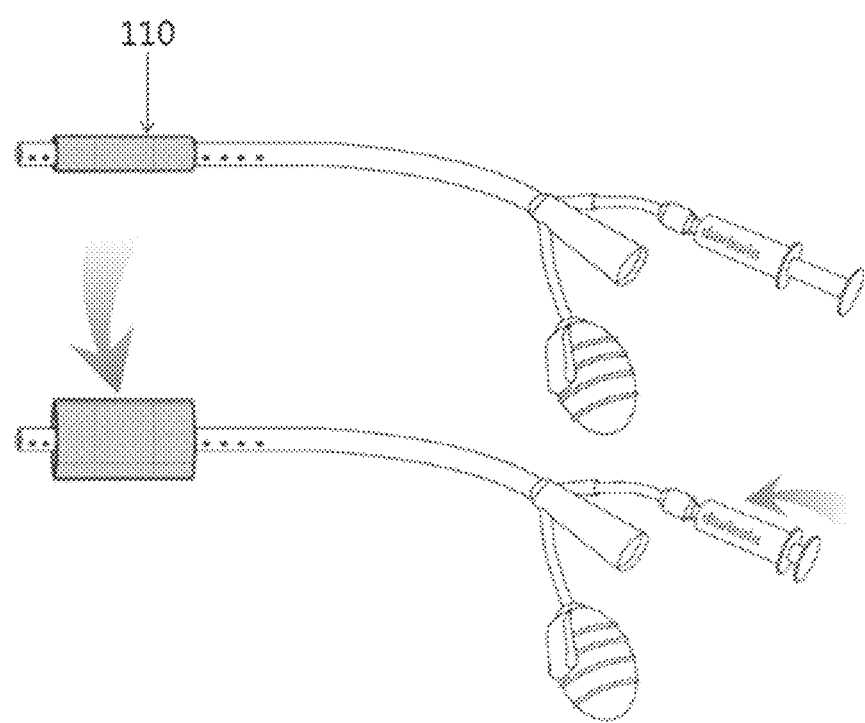
FIG. 4 shows appearances of the head filter before and after being inflated by air injection.
Figure 5:
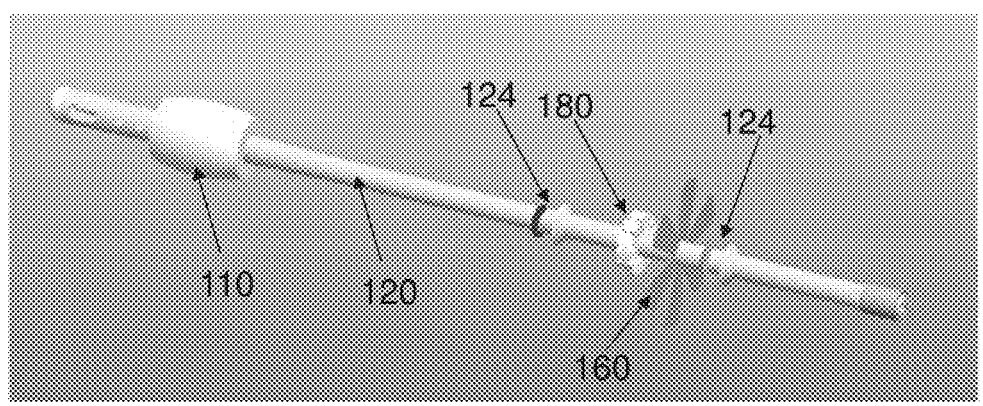
FIG. 5 is a perspective view of the device of the present invention.
Figure 6:
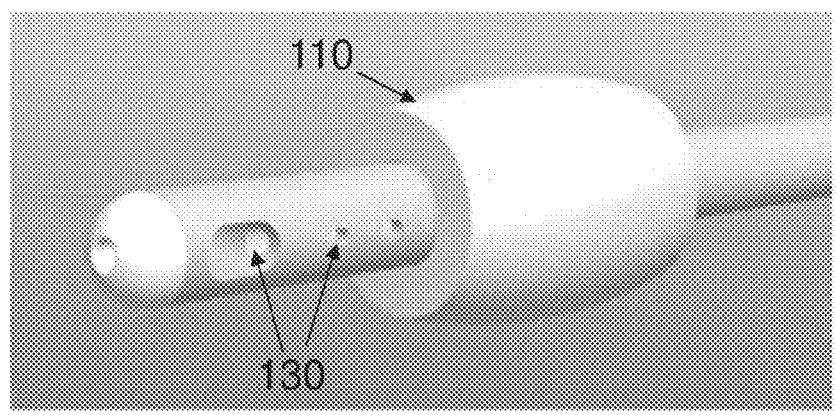
FIG. 6 is a magnified perspective view of the head portion of the main tube on which the head filter is installed.
Figure 7:
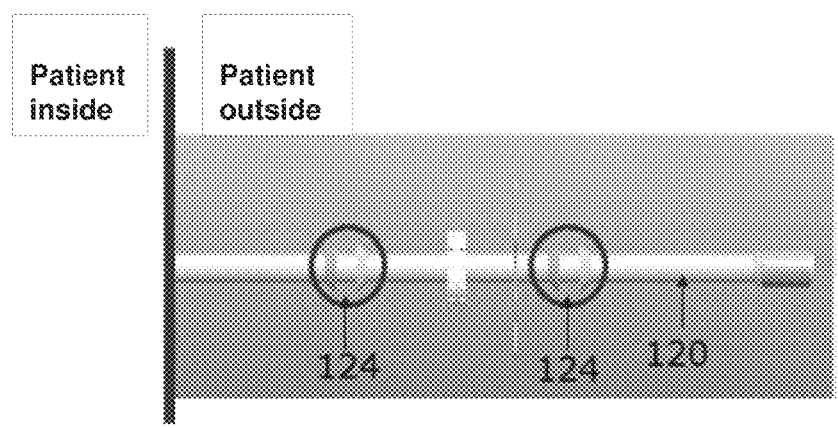
FIG. 7 shows a portion of the main tube on which a stopper or a fixing tool is installed when seen from the outside of the patient body—The stopper may be installed at a position corresponding to number 1 or 2.
Figure 8:
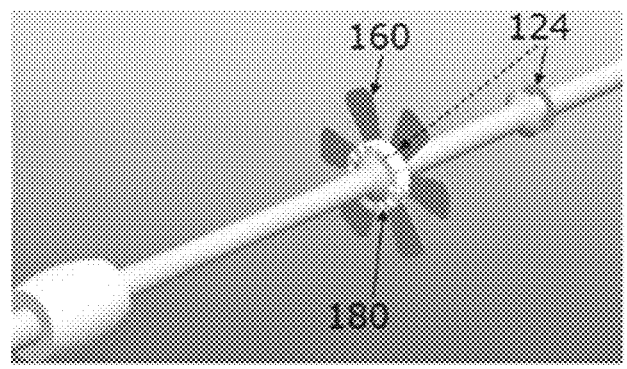
FIG. 8 shows that the stopper and the fixing tool are installed on the main tube.
Figure 9:
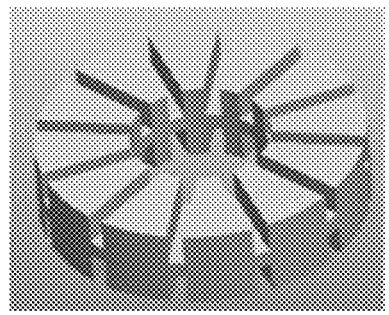
FIG. 9 shows magnified views of the stopper and the fixing tool.
Figure 9:
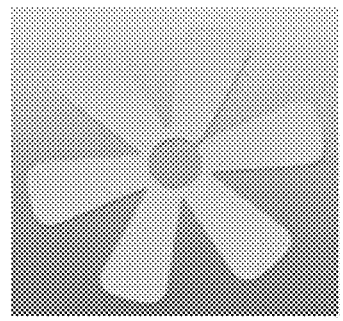
Figure 10:
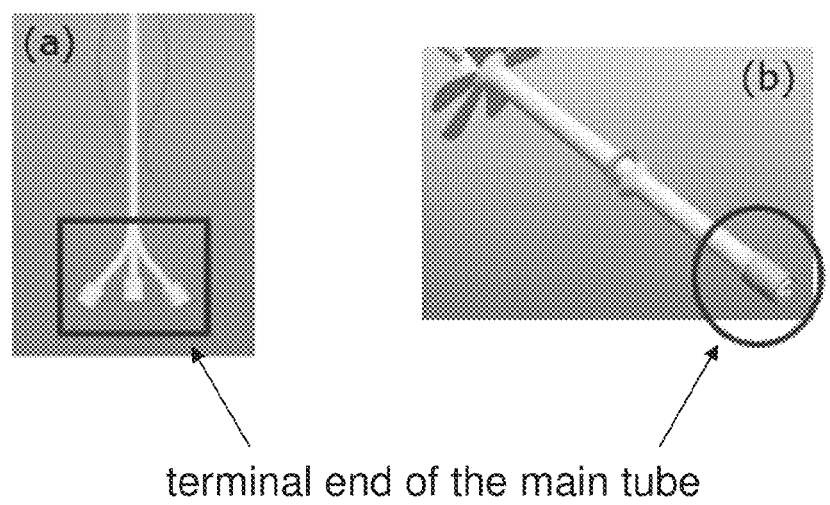
FIG. 10 shows the terminal end of the main tube—An air injector, a negative pressure pump, a storage unit connected with a drainage port for draining the intestinal contents, or the like may be installed on the terminal of the main tube. The additional apparatuses may be individually installed at respective tubes ((a) of FIG. 10), or may be installed on the main tube as a single integration shape ((b) of FIG. 10)

As shown in FIG. 4, the head filter of the present invention is designed to have a corrugated cylindrical shape with a diameter of 24 mm and a length of 30 mm before being inflated. Micro-corrugations constituting the head filter primarily prevent the intestinal contents from moving to the anastomotic area (see a FIG. in the small circle of FIG. 3). The head filter is formed integrally with the body of the main tube, and thus is not detachable from the main tube. The head filter is formed of polyurethane and thus has elasticity. Therefore, when air is injected into the head filter after the head filter is installed in the rectal tube, the head filter has a volume expansion by about 40% due to the elasticity thereof, thereby efficiently forming a barrier. The first auxiliary duct is embedded in main tube while penetrating the overall main tube, and protrudes by up to 2 cm to 3 cm from the head filter. This is for more efficient suction of the intestinal contents.

FIG. 1 shows that the head filter is placed in the intestinal canal while inflated, and the tail portion of the main tube is connected with the negative pressure pump and the syringe for air injection.

Figure 2:
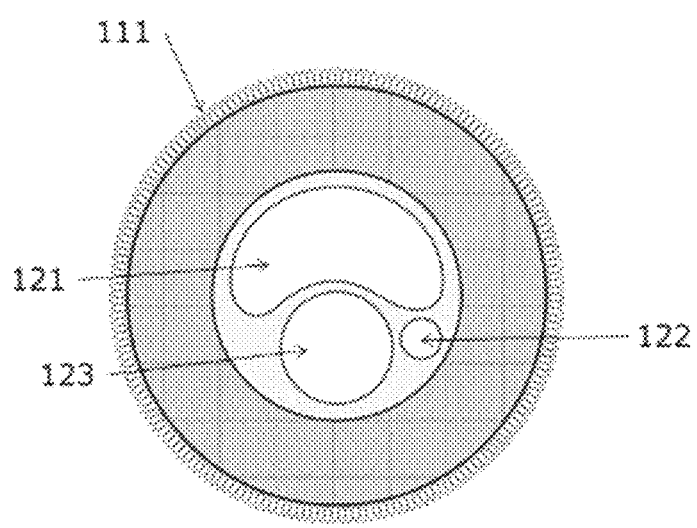
FIG. 2 shows a cross-section of a main tube.

FIG. 2 shows a cross-section of a main tube. The main tube has a triple or double lumen structure, and includes a main duct into which the intestinal contents naturally flows, a first auxiliary duct into which air can be injected for balloon dilation, and a second auxiliary duct which is connectable with the negative pressure pump. In order to install the main tube in the intestinal canal without intestinal resistance, it is preferable to form the main tube of a soft material, such as a synthetic resin. The main tube has a length of 150 mm to 300 mm. The main duct has a diameter of 12 mm to 20 mm, and the first auxiliary duct has a diameter of 8 mm to 15 mm. Both the main duct and the first auxiliary duct communicate with the head filter, and are opened (see FIG. 3). The first lumen, of which the diameter is 12 mm, directly connects the head filter and the anus and functions as a support. Primarily, the intestinal contents collected in the inflatable head filter passes through the main duct and then are directly drained out from the body. The auxiliary catheter (second auxiliary duct), of which the diameter is 8 mm, is connectable with a negative pressure pump system outside the human body, and has side holes with a diameter of approximately 4 mm. The side holes of the second auxiliary duct are connected to communicate with side holes formed in the outer circumferential surface of the main tube. Five side holes are arranged in a line on one side of the second auxiliary duct.

Thus, some of the intestinal contents, which flow into the anastomotic area while being diverted from the balloon dilation type head filter and the main duct, are secondarily sucked into main tube through the side holes formed in the body of the main tube. The auxiliary catheter is manufactured detachably from the negative pressure pump system outside the human body. When the negative pressure system outside the human body is connected to the auxiliary catheter, a negative pressure of 10-20 mmHg is formed, and thus the intestinal contents are effectively diverted from the anastomotic area and then are directly drained from the human body.

Figure 11:
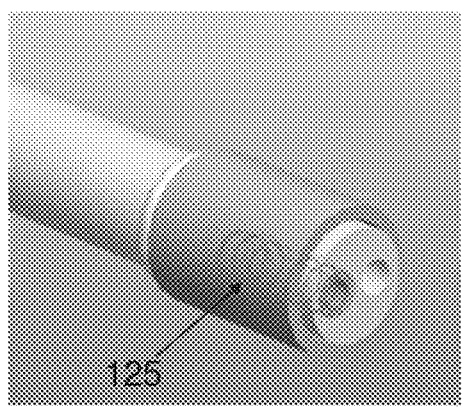
FIG. 11 shows a magnified view of the tail portion of the main tube in (b) of FIG. 10—the main tube includes a main duct in which the intestinal contents move, and a first auxiliary duct, and a check valve is installed on the terminal end of the first auxiliary duct.
Figure 11:
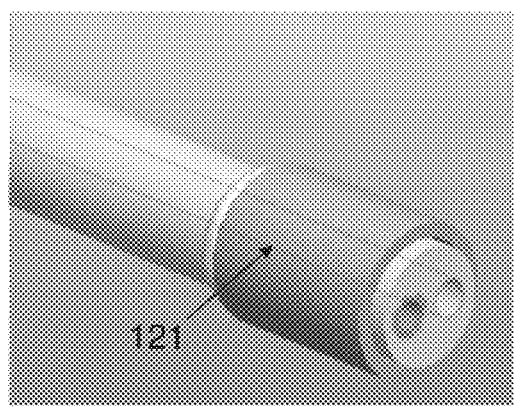
Figure 12:
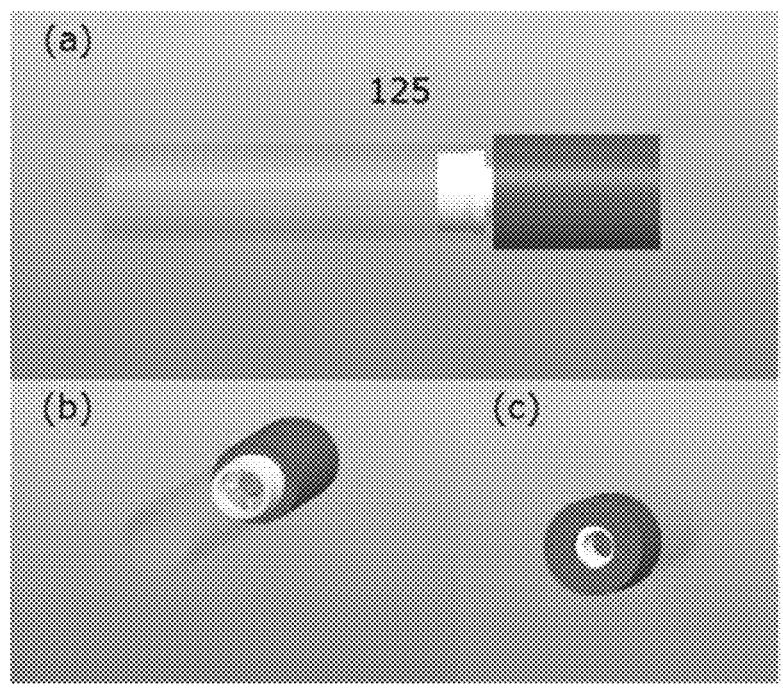
FIG. 12 shows a side view (a), an external perspective view (b), and an internal perspective view (c) of the check valve.
Figure 13:
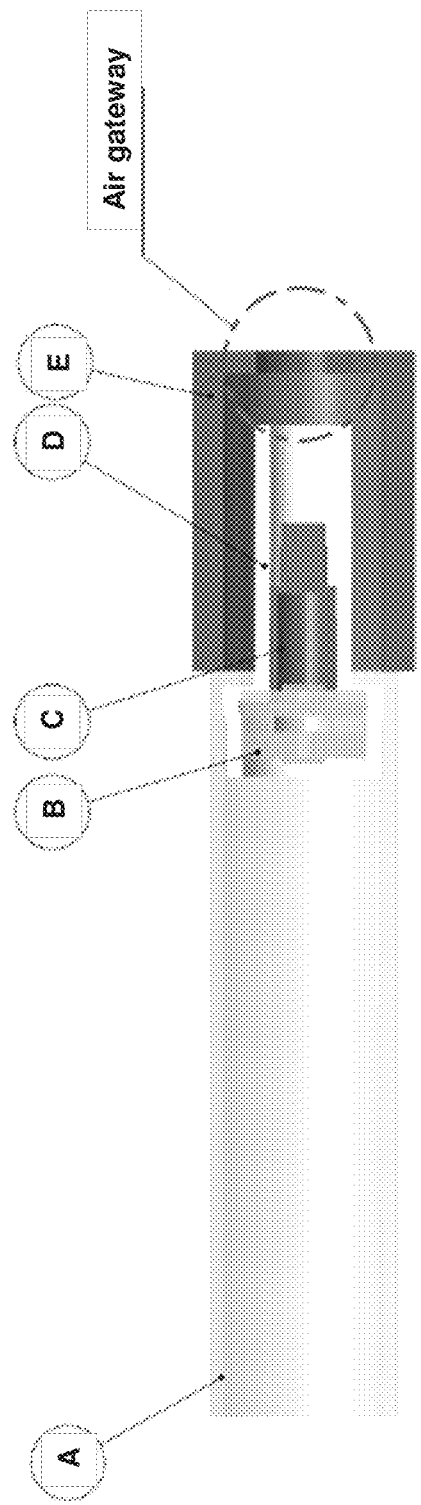
FIG. 13 shows an inner structure of the check valve—air pusher C, silicone valve B, tube A, tube holder E, and valve cover D.

FIG. 4 shows a balloon dilation procedure of the head filter. The head filter is in an inflated state before being inserted into the anus. When the main tube is inserted and placed above the rectal anastomotic area, approximately 15-20 cc of air is injected into the main tube using a general syringe outside the anus, thereby attaining the balloon dilation of the head filter. When the device is removed, the air is again sucked into the empty syringe, and thus the head filter is inflated to the original state. The air injection site of the main tube includes a backflow prevention valve, which may be configured as a check valve shown in FIGS. 11 and 12.

Figure 14:
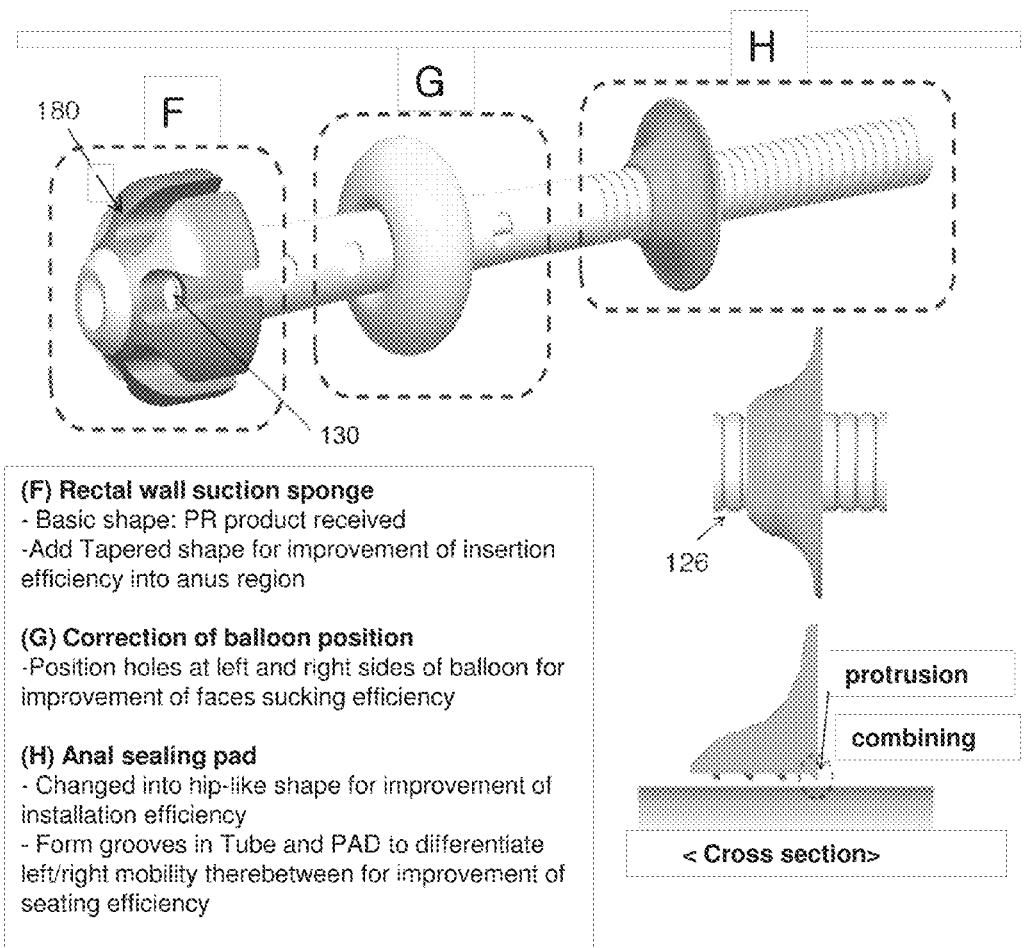
FIG. 14 shows a transformable state of a rectal anastomosis device—The rectal anastomosis device may be manufactured to have a sponge head of a smooth material as shown in the drawing. The sponge head has a function of applying a negative pressure to side holes of an anastomosis protecting stent (main tube) to prevent the intestine from being caught in the stent when the intestinal contents are sucked out. Adjunct apparatuses, such as a head filter (F) and a fixing tool (pad) (H), may be connected to the stent. G indicates a dilatable balloon, and H indicates a component functioning as a connecting ring for helping the fixation of the device of the present invention to the anus.

The device of the present invention may further include a sponge head of a smooth soft material (see FIG. 14). The function of the sponge head is to prevent the intestinal inner wall from being adsorbed onto the when the intestinal contents are sucked out by the application of the negative pressure to the side holes of the main tube. The head filter and the pad as a fixing tool are attached to the main tube. The head filter is a dilatable balloon, and the pad functions as a connecting ring for helping the fixation of the device of the present invention to the anus. The pad has a circular shape of which the center portion is concave (or convex). Protrusions are formed on the lower portion (opposite side of convex surface) of the pad or on an inner side of the pad which is in contact with the main tube, so that the pad can be combined with the grooves of the main tube.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A device for protecting rectal anastomosis, the device comprising:
    (a) a cylinder- or tube-shaped head filter which is slanted toward an outer head portion of a main tube and can be inflated by pressure, wherein the outer circumferential surface of the head filter is composed of micro-villi or micro-corrugations for preventing the inflow of the intestinal contents into an anastomotic area; and
    (b) a main tube which can be inserted inside the intestinal canal and includes a main duct, through which the intestinal contents pass, and a first auxiliary duct which transfers pressure for inflating the head filter.

2. The device of claim 1, wherein the head filter has a truncated cone shape of which the width widens toward the bottom.

3. The device of claim 1, wherein the head filter is formed of a polymeric compound.

4. The device of claim 3, wherein the polymeric compound is selected from the group consisting of polyurethane (PU), polyester (PE), polyvinylchloride (PVC), polytetrafluoroethylene (PTFE), polyethersulfone (PES), polyethylene (PE), polyetherimide (PEI), polycarbonate (PC), polyetheretherketone (PEEK), polysulfone (PS), and polypropylene (PP).

5. The device of claim 1, wherein the main tube penetrates the head filter and protrudes above the head filter.

6. The device of claim 1, wherein the main tube has side holes formed in the outer circumferential surface, wherein the intestinal contents can pass through the side holes.

7. The device of claim 6, wherein the main tube further includes a second auxiliary duct through which the intestinal contents flowing in through the side holes can pass.

8. The device of claim 6, wherein the side holes are arranged in a line on both sides of the main tube.

9. The device of claim 8, wherein the side holes arranged in a line on both sides of the main tube are alternately arranged such that the side holes neither go through each other nor face each other.

10. The device of claim 6, further comprising a radial-shaped rectal inner wall suction preventing tool installed on the foremost portion of the main tube, wherein the rectal inner wall suction preventing tool prevents the obstruction of the movement of the intestinal contents, which is caused by blocking the side holes of the main tube by the rectal inner wall.

11. The device of claim 10, wherein the rectal inner wall suction preventing tool has a cylinder shape or a tapered shape of which the width widens toward the bottom.

12. The device of claim 1, wherein the main tube has a hole communicating with an inside of the head filter, so that the intestinal contents flowing in through the head filter can be moved into the main tube.

13. The device of claim 1, wherein a backflow prevention valve is formed at the terminal end of the first auxiliary duct.

14. The device of claim 1, further comprising an air injector for inflating the head filter.

15. The device of claim 14, wherein the air injector is a syringe.

16. The device of claim 1, further comprising a negative pressure pump for providing pressure for sucking out the intestinal contents.

17. The device of claim 1, further comprising a storage unit for accommodating the intestinal contents sucked out through the main tube.

18. The device of claim 1, further comprising a fixing tool for fixing the main tube outside the intestinal canal.

19. The device of claim 18, wherein the fixing tool is a radial-shaped sticker having an adhesive surface or a pad combinable with the main tube.

20. The device of claim 18, further comprising a stopper for preventing the up-and-down movement of the radial-shaped sticker.

* * * * *